(12) United States Patent
Seto

(10) Patent No.: US 7,072,437 B2
(45) Date of Patent: Jul. 4, 2006

(54) RADIATION TOMOGRAPHY SYSTEM AND TOMOGRAPHY METHOD

(75) Inventor: Masaru Seto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/016,948

(22) Filed: Dec. 20, 2004

(65) Prior Publication Data

US 2005/0152493 A1 Jul. 14, 2005

(30) Foreign Application Priority Data

Dec. 26, 2003 (JP) ............................. 2003-433889

(51) Int. Cl.
*G21K 1/12* (2006.01)
*H05G 1/60* (2006.01)
*G01N 23/00* (2006.01)
*A61B 6/00* (2006.01)

(52) U.S. Cl. ..................... 378/20; 378/98.5; 378/162

(58) Field of Classification Search ............. 378/4, 378/15, 18, 19, 98.7, 98.8, 108, 109, 97, 378/16, 20, 131, 132, 130, 98, 146, 98.5, 378/162; 382/132

See application file for complete search history.

(56) References Cited

U.S. PATENT DOCUMENTS

| | | | |
|---|---|---|---|
| 3,770,963 A | 11/1973 | Vandervelden et al. | |
| 3,842,280 A | 10/1974 | Herrick | |
| 3,974,385 A | 8/1976 | Grim | |
| 4,297,638 A | 10/1981 | LaFrance | |
| 4,311,913 A | 1/1982 | Resnick et al. | |
| 4,386,320 A | 5/1983 | LaFrance | |
| 4,918,714 A | 4/1990 | Adamski et al. | |
| 4,991,193 A | 2/1991 | Cecil et al. | |
| 5,008,916 A | 4/1991 | Le Guen | |

(Continued)

FOREIGN PATENT DOCUMENTS

EP 1393681 A1 3/2004

(Continued)

OTHER PUBLICATIONS

European Search Report; Berlin; Mar. 9, 2005; EP04257985; 4 pgs.

(Continued)

*Primary Examiner*—Edward J. Glick
*Assistant Examiner*—Irakli Kiknadze
(74) *Attorney, Agent, or Firm*—Carl B. Horton, Esq.; Armstrong Teasdale LLP

(57) ABSTRACT

A radiation tomography system includes a radiation source and a radiation detector opposed to the radiation source with a subject between them. The radiation tomography system further includes a scanner that scans a subject by moving the radiation source and radiation detector while rotating them about the subject; a calculator that calculates a control value with which an exposure of a radiation emanating from the radiation source is controlled; and a display on which at least one of calculated control values associated with positions in the direction of rotation of the scanner and control values associated with positions in the direction of a body axis linking the subject's head and the subject's tiptoe is displayed in relation to the respective pieces of positional information on the subject.

17 Claims, 5 Drawing Sheets

U.S. PATENT DOCUMENTS

| | | | |
|---|---|---|---|
| 6,363,134 B1 * | 3/2002 | Suzuki | 378/15 |
| 6,377,656 B1 * | 4/2002 | Ueki et al. | 378/98.7 |
| 6,404,844 B1 * | 6/2002 | Horiuchi et al. | 378/8 |
| 6,449,337 B1 | 9/2002 | Honda et al. | |
| 6,490,337 B1 * | 12/2002 | Nagaoka et al. | 378/20 |
| 6,870,898 B1 * | 3/2005 | von der Haar | 378/97 |
| 2003/0016778 A1 | 1/2003 | Tachizaki et al. | |

FOREIGN PATENT DOCUMENTS

| | | |
|---|---|---|
| JP | 54140492 A * | 10/1979 |
| JP | 2001-231775 | 8/2001 |
| JP | 2002-177261 | 6/2002 |
| WO | WO-02/071946 A1 | 9/2002 |

OTHER PUBLICATIONS

Christoph Suess, Xiaoyan Chen; "Dose Optimization in Pediatric CT: Current Technology and Future Innovations"; Pediatr Radiol (2002) 32:729-734.

Bryan R. Westerman; "Radiation Dose from Toshiba CT Scanners"; Pediatr Radiol (2002) 32:735-737.

Y. Kawabuchi, Patent Application "Thermal Generator Assembly, X-Ray Imaging System, and X-Ray Apparatus Overheat Preventing Method" filed Oct. 7, 2004, 22 pgs.

* cited by examiner

RADIATION TOMOGRAPHY SYSTEM AND TOMOGRAPHY METHOD

CROSS REFERENCE TO RELATED APPLICATIONS

This application claims the benefit of Japanese Application No. 2003-433889 filed Dec. 26, 2003.

BACKGROUND OF THE INVENTION

The present invention relates to a radiation tomography system and a tomography method. More particularly, the present invention is concerned with a radiation tomography system and a tomography method that display a control value with which an exposure of X-rays radiated from an X-ray source is controlled.

As a modality for producing tomographic images, for example, X-ray computed tomography (CT) systems are known. The X-ray CT system irradiates, for example, X-rays as a radiation, detects X-rays having passed through a subject, and produces tomographic images through calculation.

The X-ray CT system includes a scanner gantry composed of an X-ray tube and a detector array opposed to the X-ray tube with a subject between them. The detector array detects X-rays irradiated from the X-ray tube to the subject. The X-ray CT system moves the scanner gantry while rotating it about the subject, and thus scans the subject in a direction parallel to the direction of a body axis linking the subject's head and the subject's tiptoe. Consequently, a plurality of views of projection data is produced. The X-ray CT system recomposes acquired projection data to produce tomographic images of a predetermined slice thickness representing the subject.

A facility is known for automatically controlling a control value with which an exposure of X-rays radiated from the X-ray tube is controlled, for example, a value of a tube current to be fed to the X-ray tube according to a scanned position in a subject. Known as an X-ray CT system including the facility is a system that calculates tube current values, which are associated with regions whose X-ray absorption doses are different from one another, for each turn, and displays the calculated tube current values in the form of a text or a graph (refer to, for example, Patent Document 1).

However, according to Patent Document 1, the calculated tube current values are displayed as discrete values calculated for each turn of the scanner gantry in association with positions in the body-axis direction. Consequently, a user cannot check the tube current values to be attained during each turn.

Moreover, when a helical scan is performed, that is, when reconstructed images are inconsistent with turns, or when a turn out of turns made by the scanner gantry during which certain image data has been acquired is hardly identified due to adoption of a multi-slice imaging technique, it is hard to identify a tube current value used to reconstruct an image.

[Patent Document 1] Japanese Unexamined Patent Application Publication No. 2002-177261

SUMMARY OF THE INVENTION

Therefore, an object of the present invention is to provide a radiation tomography system and a tomography method that simplify checking and adjusting of a control value for an exposure and thus improve maneuverability.

In order to accomplish the above object, a radiation tomography system in accordance with the present invention comprises a radiation source and a radiation detector opposed to the radiation source with a subject between them. Furthermore, the radiation tomography system comprises: a scanning means for scanning a subject by moving at least one of the radiation source and radiation detector while rotating it about the subject; a control value calculating means for calculating a control value with which an exposure of a radiation emitted from the radiation source is controlled; and a display means for displaying at least one of control values, which are calculated in association with positions in the direction of rotation in which the scanning means rotates, and control values, which are calculated in association with positions in the direction of a body axis linking the subject's head and the subject's tiptoe, in relation to the respective pieces of positional information on the subject.

According to the radiation tomography system of the present invention, at least one of the control values associated with positions in the direction of rotation of the scanning means and those associated with positions in the body-axis direction is displayed in relation to respective pieces of positional information on the subject. This facilitates checking of control values.

In order to accomplish the foregoing object, a tomography method in accordance with the present invention is adapted to a radiation tomography system comprising a radiation source and a radiation detector opposed to the radiation source with a subject between them. The tomography method comprises: a step of calculating a control value with which an exposure of a radiation emanating from the radiation source is controlled; a step of displaying a change of calculated control values in association with pieces of positional information on the subject in at least one of the direction of rotation, in which the radiation source and radiation detector rotate, and the direction of a body axis linking the subject's head and the subject's tiptoe; and a step of scanning the subject by moving at least one of the radiation According to the tomography method of the present invention, a control value with which an exposure of a radiation emanating from the radiation source is controlled is calculated.

Thereafter, a change of calculated control values is displayed in association with respective pieces of positional information on the subject in at least one of the direction of rotation in which the radiation source and radiation detector rotate and the body-axis direction.

Thereafter, the radiation source and radiation detector are moved while being rotated about the subject in order to scan the subject.

According to the radiation tomography system of the present invention, maneuverability can be improved by simplifying checking and adjusting of a control value to be used to control a radiation exposure.

According to the tomography method of the present invention, maneuverability can be improved by simplifying checking and adjusting of a control value to be used to control a radiation exposure.

Further objects and advantages of the present invention will be apparent from the following description of the preferred embodiments of the invention as illustrated in the accompanying drawings.

DETAILED DESCRIPTION OF THE INVENTION

Referring to drawings, the best mode for implementing the present invention will be described below.

Figure 1:
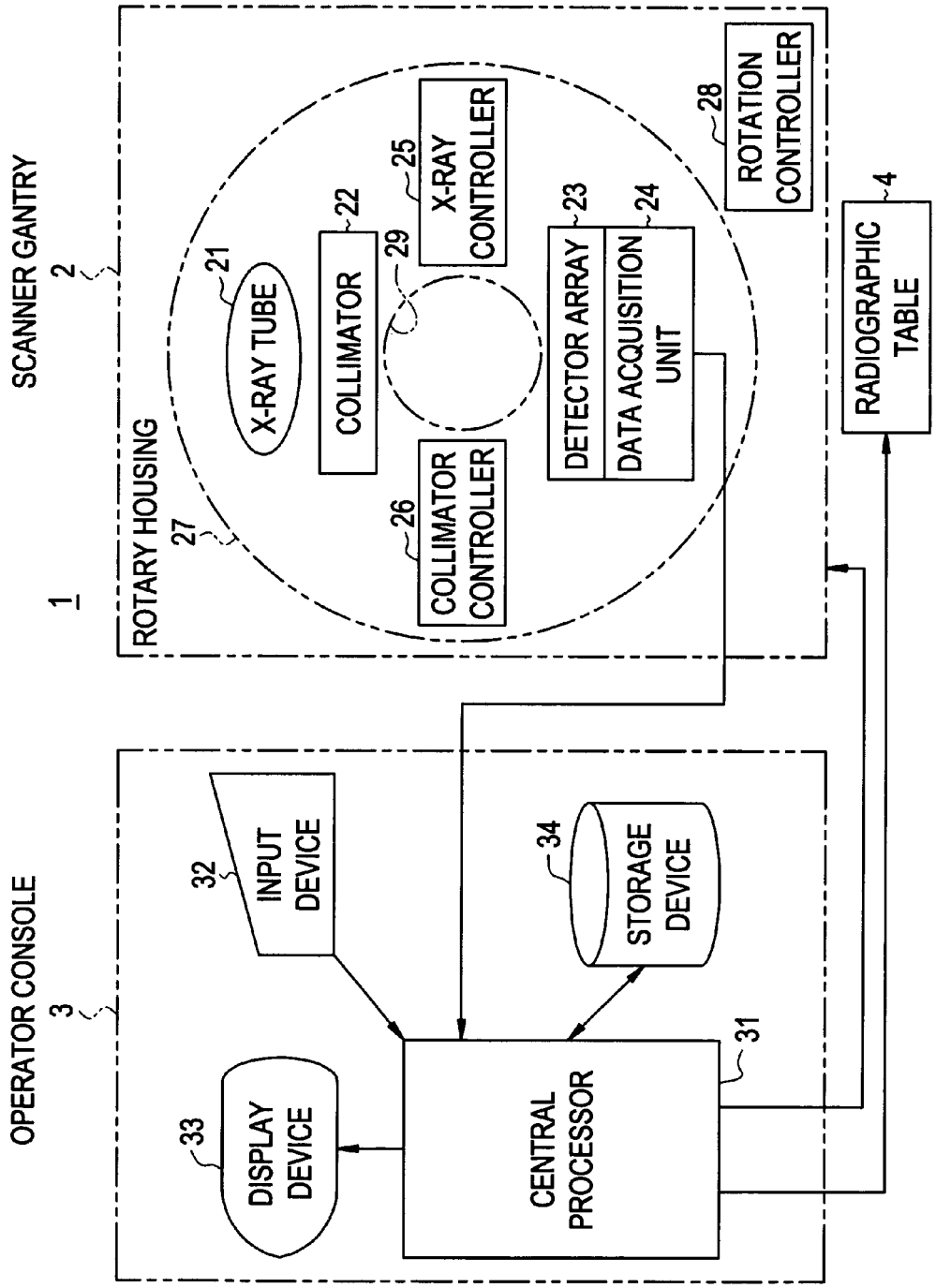
FIG. 1 is a block diagram illustratively showing an X-ray CT system 1 in accordance with an embodiment of the present invention.

FIG. 1 is a block diagram showing the overall configuration of an X-ray CT system 1 in accordance with the present invention. An example of a radiation tomography system in accordance with the present invention is equivalent to the X-ray CT system 1 that adopts X-rays as a radiation.

As shown in FIG. 1, the X-ray CT system 1 comprises a scanner gantry 2, an operator console 3, and a radiographic table (cradle) 4.

The scanner gantry 2 includes an X-ray tube 21, a collimator 22, a detector array 23, a data acquisition unit 24, an X-ray controller 25, and a collimator controller 26. An example of a scanning means included in the present invention is equivalent to the scanner gantry 2. The scanner gantry 2 scans a subject while moving in a direction parallel to the direction of a body axis linking the subject's head and the subject's tiptoe.

The X-ray tube 21 radiates X-rays. X-rays radiated from the X-ray tube 21 are recomposed by the collimator 22, and irradiated to the detector array 23. An example of a radiation source included in the present invention is equivalent to the X-ray tube 21.

The detector array 23 is, for example, a multi-array detector having a plurality of X-ray detector elements set in array two-dimensionally. An example of a radiation detector included in the present invention is equivalent to the detector array 23.

The detector array 23 forms an X-ray incidence surface curved like a semi-cylindrical concave surface as a whole. The detector array 23 comprises combinations of, for example, a scintillator and a photodiode. The present invention is not limited to the combinations. Alternatively, semiconductor detection elements utilizing cadmium telluride (CdTe) or the like or ionization chamber-type X-ray detection elements utilizing a xenon gas will do. The detector array 23 is connected to the data acquisition unit 24.

The data acquisition unit 24 acquires detection data provided by each of the X-ray detection elements constituting the detector array 23. The data acquisition unit 24 transmits collected detection data to a central processor 31 that will be described later.

The X-ray controller 25 controls X-irradiation from the X-ray tube 21.

The collimator controller 26 controls the collimator 22.

The illustrations of the relationships of connection between the X-ray tube 21 and X-ray controller 25 and between the collimator 22 and collimator controller 26 will be omitted.

The X-ray tube 21, collimator 22, detector array 23, data acquisition unit 24, X-ray controller 25, and collimator controller 26 are incorporated in a rotary housing 27 of the scanner gantry 22. Incidentally, the subject is asked to lie down on the cradle in a bore 29 located in the center of the rotary housing 27.

The rotary housing 27 is rotated while being controlled by a rotation controller 28. In the rotary housing 27, the X-ray tube 21 radiates X-rays and the detector array 23 detects X-rays which have passed through the subject, as each view of projection data. Incidentally, the connection between the rotary housing 27 and rotation controller 28 will be omitted.

The operator console 3 includes the central processor 31, an input device 32, a display device 33, and a storage device 34.

The central processor 31 comprises, for example, a CPU, programs, and a memory. The central processor 31 controls the movement of the scanner gantry 2 according to the programs stored in the storage device 34. Moreover, the central processor 31 has at least ability to acquire projection data produced based on X-rays that have passed through the subject and that are detected by the detector array 23, and ability to reconstruct tomographic images of the subject according to the acquired projection data. Calculation and adjustment of a control value to be performed by the central processor 31 will be described later.

The central processor 31 is connected to each of the display device 33, input device 32, and storage device 34.

Tomographic image information, calculated tube current values, and adjusted tube current values that are provided by the central processor 31 are displayed on the display device 33. The other information is also displayed on the display device 33.

A user manipulates the input device 32 so as to transmit various instructions and pieces of information to the central processor 31.

rojection data, tomographic image information, and settings or conditions provided from the central processor 31 are stored in the storage device 34.

A user uses the display device 33 and input device 32 to operate the X-ray CT system bi-directionally.

Figure 2:
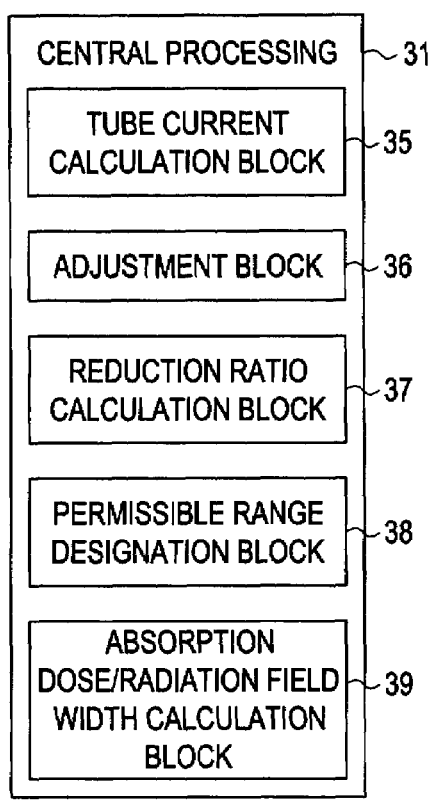
FIG. 2 is a block diagram illustratively showing a central processor 31 included in the X-ray CT system 1 shown in FIG. 1.

FIG. 2 is a block diagram showing an example of the configuration of the central processor 31.

The central processor 31 comprises a tube current calculation block 35, an adjustment block 36, a reduction ratio calculation block 37, a permissible range designation block 38, an absorption dose/radiation field width calculation block 39. The present embodiment adopts a value of a tube current, which is supplied to the X-ray tube, as a control value to be used to control an exposure.

The tube current calculation block 35 calculates an ellipticity of a section of the subject, who lies at each of predetermined positions, on the basis of the width and thickness of the subject body using projection data acquired through scout radiography. Moreover, the tube current calculation block 35 calculates the sectional area of the subject on the basis of an amount of attenuated X-ray radiation. Based on these calculated data items, tube current values associated with positions in the direction of rotation in which the scanner gantry 2 is rotated and in a scanning direction are calculated. The tube current calculation block 35 transmits the calculated tube current values to each of the display device 33 and storage device 32. Incidentally, an example of a control value calculating means included in the present invention is equivalent to the tube current calculation block 35.

The adjustment block 36 receives a tube current value that is associated with a predetermined value and which a user has modified using the display device 33 and input device 32. The adjustment block 36 fits the modified tube current value to the tube current values calculated by the tube current calculation block 35. Moreover, the adjustment block 36 calculates tube current values associated with positions near the predetermined position so that the modified tube current value will be continuous to the calculated tube current values, and transmits the calculated tube current values to each of the display device 33 and storage device 34. Incidentally, an example of an adjusting means included in the present invention is equivalent to the adjustment block 36.

The reduction ratio calculation block 37 compares the calculated tube current values, that is, first tube current values stored in the storage device 34 by the tube current calculation block 35 with the adjusted tube current values, that is, second tube current values stored in the storage device 34 after the adjustment block 36 adjusts the first tube current values. The reduction ratio calculation block 37 calculates reduction ratios of the second tube current values to the first tube current values, and transmits the reduction ratios to each of the storage device 34 and display device 33. Incidentally, an example of a reduction ratio calculating means included in the present invention is equivalent to the reduction ratio calculation block 37.

The permissible range designation block 38 designates an upper limit and a lower limit for each of an absorption dose and a width of a radiation field which a user enters at the input device 32. The permissible range designation block 38 transmits the designated values to each of the storage device 34 and display device 33. Incidentally, an example of a permissible range designating means included in the present invention is equivalent to the permissible range designation block 38.

Based on the tube current values stored in the storage device 34 by the tube current calculation block 35 or adjustment block 36, the absorption dose/radiation field width calculation block 39 calculates an absorption dose and a radiation field width to be attained during one scan or one turn made by the scanner gantry 2 so that the absorption dose and radiation field width will fall within the ranges designated by the permissible range designation block 38. The absorption dose/radiation field width calculation block 39 transmits the calculated values of the absorption dose and radiation field width to each of the display device 33 and storage device 34. Incidentally, an example of an absorption dose/radiation field width calculating means included in the present invention is equivalent to the absorption dose/radiation field width calculation block 39.

Next, the actions to be performed in the X-ray CT system 1 in accordance with the present invention will be described in conjunction with drawings below.

Figure 3:
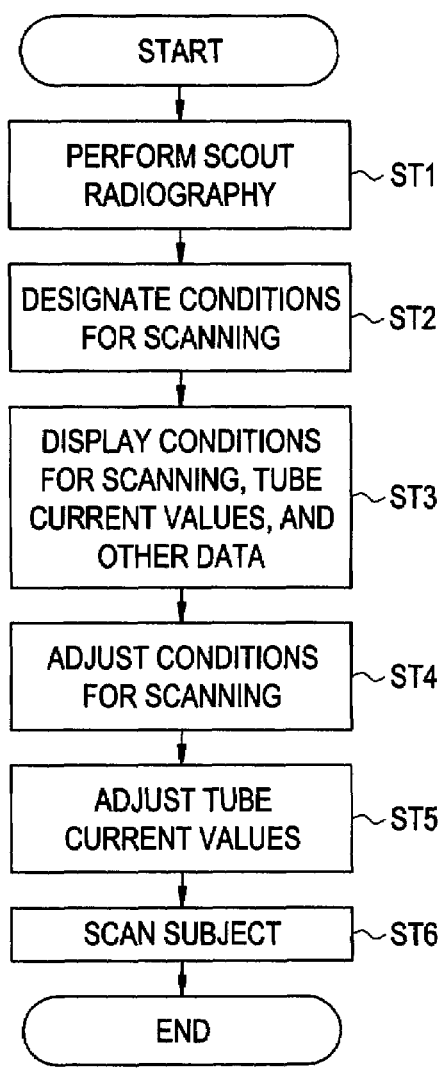
FIG. 3 is a flowchart describing the actions to be performed in the X-ray CT system 1 shown in FIG. 1.

FIG. 3 is a flowchart describing the actions to be performed in the X-ray CT system 1 in accordance with the present invention. The tomography method in accordance with the present invention is adapted to the X-ray CT system 1 in accordance with the present invention.

To begin with, a user uses the input device 32 to designate a direction in which scout radiography is performed and a range within which the scout radiography is performed. Scout radiography is performed within the designated range (ST1). According to the present embodiment, for example, a scout image representing a sagittal section of the subject is produced.

The central processor 31 controls the scanner gantry 2 so that the scanner gantry will scan the subject within a predetermined range in a predetermined direction according to the designated conditions. At this time, for example, the scanner gantry 2 moves in the body-axis direction of the subject with the X-ray tube 21 and detector array 23 held at certain positions but not rotated. The detector array 23 transmits detected data to the central processor 31 via the data acquisition unit 24. The central processor 31 produces a scout image according to the acquired data, and transmits it to the display device 33.

Thereafter, the user views the scout image of the subject displayed on the display device 33, and designates conditions for scanning (ST2).

The user uses, for example, the input device 32 to enter a scan start position, a scan end position, an image production interval, and a slice thickness. The tube current designation block 36 included in the central processor 31 references the projection data representing the scout image and the conditions for scanning entered at the input device 32 so as to calculate tube current values. The central processor 31 transmits the received conditions for scanning and the calculated tube current values to the display device 33.

Moreover, the user uses the input device 32 to enter a permissible absorption dose of X-rays irradiated during one scan or one turn and a permissible radiation field width. The permissible absorption dose and radiation field width are transferred to the permissible range designation block 38. The X-ray absorption dose and radiation field width are determined for each region to be radiographed. At the same time, the user also designates a scan field and conditions for image reconstruction.

Thereafter, the conditions for scanning entered by the user and the tube current values calculated by the central processor 31 are displayed on the display device 33 (ST3).

Figure 4:
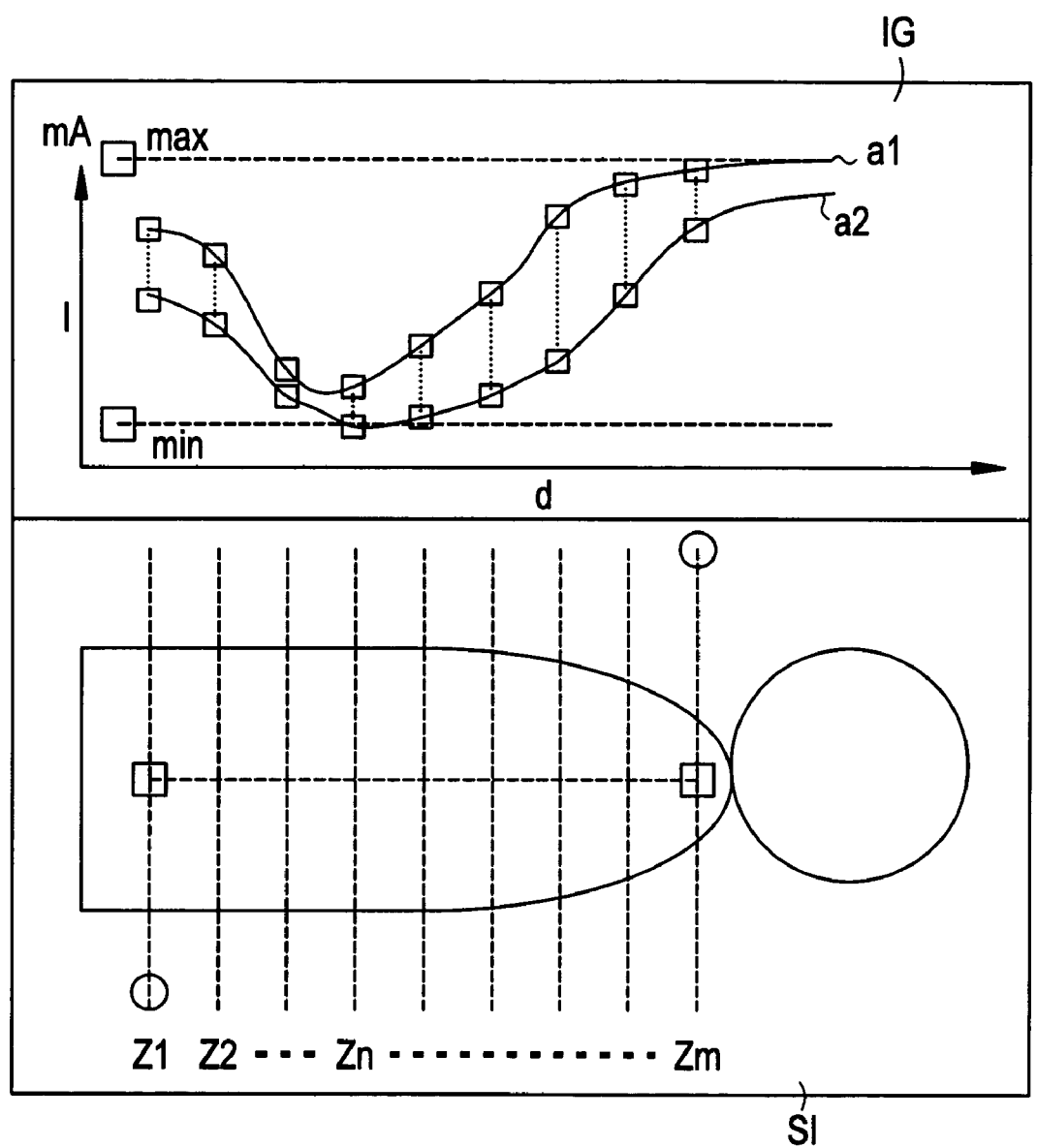
FIG. 4 is a schematic view showing an example of display made on a display device 33 included in the X-ray CT system 1 shown in FIG. 1.

FIG. 4 is a schematic view showing an example of display of a scout image S1 and tube current data IG on the display device 33.

As shown in FIG. 4, image production positions Z1 to Zm are indicated in relation to the scout image S1 of the subject produced at step ST1.

Moreover, on the scout image S1 so as to correspond to the image production positions Z1 to Zm, successive tube current values associated with positions in a scanning direction in which one scan is performed are indicated in the form of a graph that indicates current values I along an axis of ordinates and that indicates distances d along an axis of abscissas. Herein, one scan shall continue from the instant irradiation of X-rays from the X-ray tube 21 is started to the instant the irradiation is terminated. According to the present embodiment, the scanning direction shall be a direction parallel to the body-axis direction of the subject. Furthermore, the graph indicates a maximum tube current value max and a minimum tube current value min out of various tube current values to be attained during one scan, and a maximum tube current value a1 and a minimum tube current value a2 out of various tube current values to be attained during one turn of the scanner gantry 2. Herein, the scanner gantry 2 shall be rotated in the scanning direction, that is, the direction orthogonal to the body-axis direction of the subject.

Now, when the user selects any point on the graph or any image production position, the absorption dose/radiation field width calculation block 39 included in the central processor 31 calculates an absorption dose and a radiation field width, which are attained during each turn of the scanner gantry 2, on the basis of the designated permissible range and the tube current value associated with the selected position, and transmits the calculated values to the display device 33. Consequently, the user can check the absorption dose and radiation field width.

Figure 5:
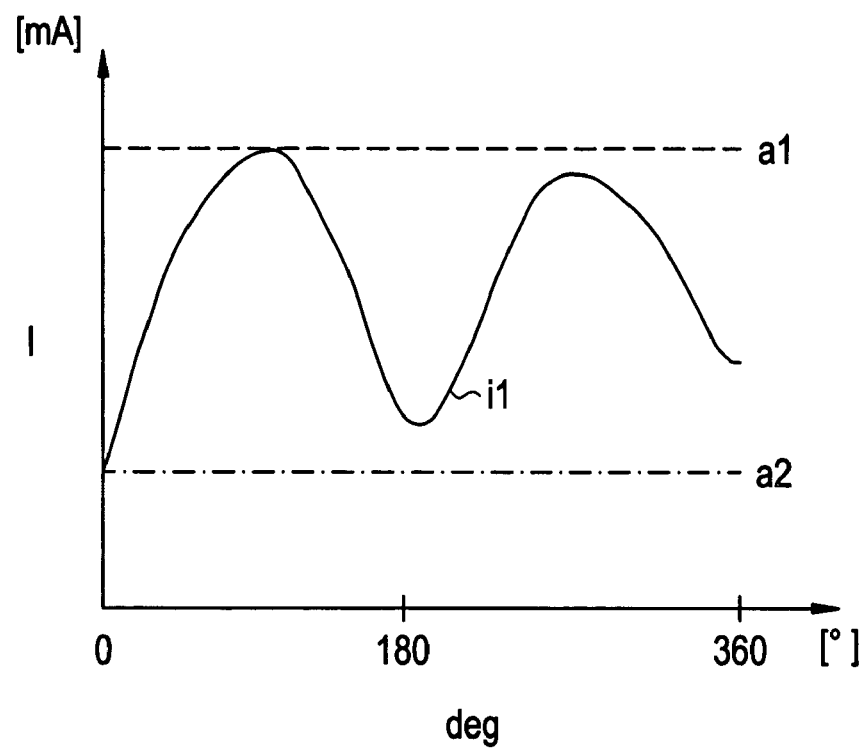
FIG. 5 shows a graph presenting an example of display of tube current values in association with positions in the direction of rotation of a scanner gantry 2 included in the X-ray CT system 1 shown in FIG. 1.

FIG. 5 is a schematic view showing an example of display of tube current data representing tube current values associated with positions in the direction of rotation of the scanner gantry. The axis of ordinates indicates the tube current values 1, and the axis of abscissas indicates, for example, angles of rotation deg. Herein, when the X-ray tube 21 irradiates X-rays in a direction perpendicular to the subject, the angle of rotation shall be 0°.

Once the user selects a predetermined image production position, that is, an image production position Zn shown in FIG. 4, the tube current data shown in FIG. 5 is displayed on part of the display device.

The tube current values I to be associated with the image production positions Zn and attained at the angles of rotation of about 0° and 180° during one turn made by the scanner gantry 2 are set to small values. The tube current values I to be attained at the angles of rotation of about 90° or 270° are set to large values. This is attributable to the fact that assuming that a section of a subject orthogonal to the body axis thereof is elliptic, an X-ray absorption rate in the direction of the minor axis of the ellipse is different from that in the direction of the major axis thereof. Moreover, the maximum tube current value a1 and minimum tube current value a2 to be attained during one turn are also displayed. Furthermore, when the user selects any point on the graph shown in FIG. 5, the absorption dose/radiation field width calculation block 39 included in the central processor 31 calculates an optimal absorption dose and an optimal radiation field width according to the tube current values shown in FIG. 4 and FIG. 5 and the permissible range designated in advance, and then transmits the calculated values to the display device 33.

An example of a displaying step included in the present invention is equivalent to step ST3.

Thereafter, a scanned position is adjusted if necessary (ST4).

The user uses the input device 32 to adjust, if necessary, the scan start position, scan end position, and image production interval displayed on the display device 33. Moreover, for example, the user may select any image production position shown in FIG. 4 using a cursor or the like, and drag a line representing the image production position. Otherwise, the user may use the input device 32 to enter a numerical value representing a scan start position.

Thereafter, calculated and displayed tube current values are adjusted (ST5).

Figure 6:
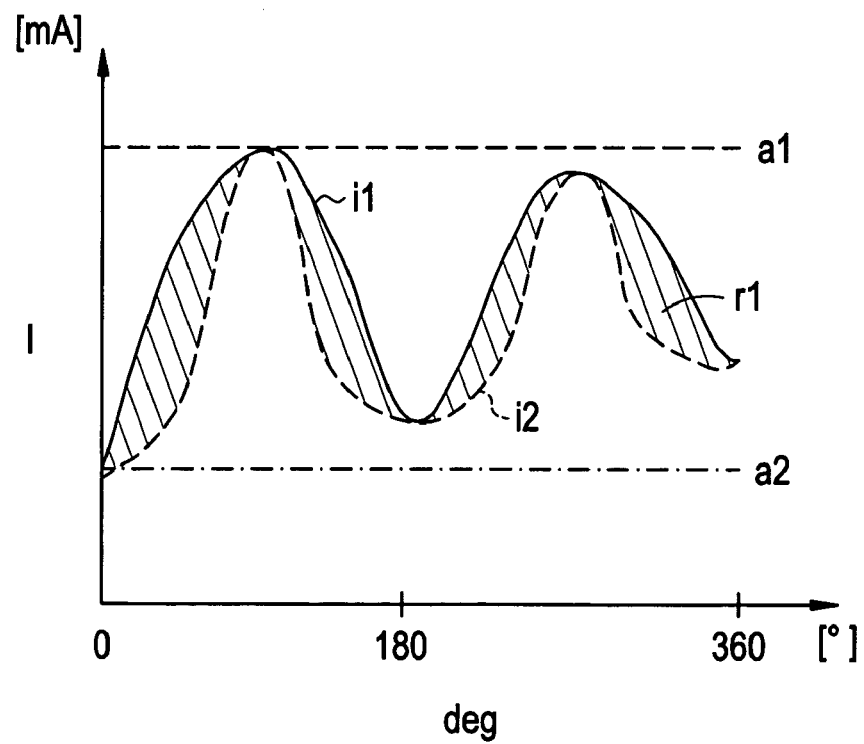
FIG. 6 shows a graph indicating tube current values produced by adjusting the tube current values shown in FIG. 5.

FIG. 6 shows a graph indicating the relationship between a tube current value associated with a position in the direction of rotation of the scanner gantry and an angle of rotation.

For example, the user selects any point on a graph i1 indicating tube current values as shown in FIG. 5 using a cursor or the like displayed on the display device 33, and drags the graph until the point indicates a predetermined tube current value. Herein, when X-rays are irradiated to a subject in an anterior or posterior direction, that is, at an angle of about 0° or 180°, the intensity of the X-rays is low. When X-rays are irradiated to a subject in a lateral direction, that is, at an angle of about 90° or 270°, the intensity of the X-rays is high. Therefore, the user adjusts or reduces tube current values associated with intermediate angles between the angles at which the intensity of X-rays is high or low.

Consequently, the graph i1 indicating the calculated tube current values as shown in FIG. 5 is adjusted to become a graph i2 shown in FIG. 6. Compared with a case where the calculated tube current values are adopted, an X-ray exposure can be reduced by a degree equivalent to a value contained in a domain r1 indicated with a hatched area of FIG. 6. The reduction ratio calculation block 37 included in the central processor 31 performs the foregoing calculation of a reduction ratio on the basis of data displayed on the display device 33.

Moreover, the user may vertically drag a broken line indicating the maximum tube current value a1 or minimum tube current value a2 above or below the graph so as to adjust tube current values. Otherwise, after any point on the graph is pointed out, a numerical value may be entered at the input device 32. The absorption dose/radiation field width calculation block 39 included in the central processor 31 calculates an appropriate absorption dose and an appropriate radiation field width according to the adjusted tube current values and the permissible range designated in advance. When the user selects any point on the graph indicating the adjusted tube current values, the central processor 31 displays the calculated absorption dose and radiation field width on the display device 33.

When the adjustment is completed, the user uses the input device 32 to enter an adjustment completion command. The adjustment completion command is transferred to the central processor 31. After the user confirms the displayed absorption dose and tube current values, the user can start a scan.

Incidentally, an example of an adjusting step included in the present invention is equivalent to step ST5.

For determination of the above settings, the user manipulates the input device 32 while viewing an image displayed on the display device 33. The settings are then stored in the storage device 34 via the central processor 31.

Thereafter, a scan is performed under the determined conditions for scanning (ST6).

The central processor 31 transmits commands to each of the scanner gantry 2 and radiographic table 4 according to a program which is stored in the storage device 34 and to which the above modified descriptions are added. Consequently, the scanner gantry 2 scans the subject along the body axis of the subject, who lies down at a predetermined position, from the scan start position to the scan end position at a determined scanning velocity while rotating in a direction orthogonal to the body axis. The detector array 23 transmits detected projection data to the central processor 31 via the data acquisition unit 24. The central processor 31 stores the received data in the storage device 34. In the present invention, both of the axial and helical scan techniques can be adopted.

An example of a scanning step included in the present invention is equivalent to step ST6.

Thereafter, the central processor 31 reconstructs images under the designated conditions using the projection data acquired at step ST6.

The central processor 31 executes reconstruction according to a program such as a back projection program stored in the storage device 34. The central processor 31 displays tomographic images, which represent sections defined with the designated image production positions, on the display device 33.

Incidentally, a method of displaying tube current values is not limited to the foregoing one. Alternatively, a method described below may be adopted.

Figure 7:
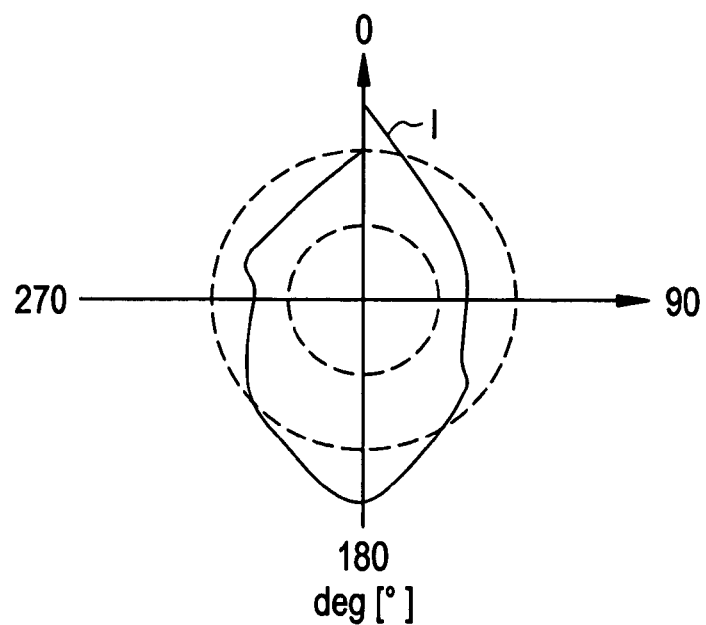
FIG. 7 shows a graph presenting another example of display of tube current values in association with positions in the direction of rotation of the scanner gantry 2 included in the X-ray CT system 1 shown in FIG. 1.

FIG. 7 shows a graph presenting another example of display of tube current values associated with positions on a plane of rotation on which the scanner gantry is rotated. As shown in FIG. 7, the axes of ordinates and abscissas indicate angles, and tube current values associated with respective angles of rotation are indicated. Referring to FIG. 7, for example, a tube current value indicated with a point located closer to the center of a coordinate plane is smaller, and a tube current value indicated with a point located farther from the center thereof is larger.

Figure 8:
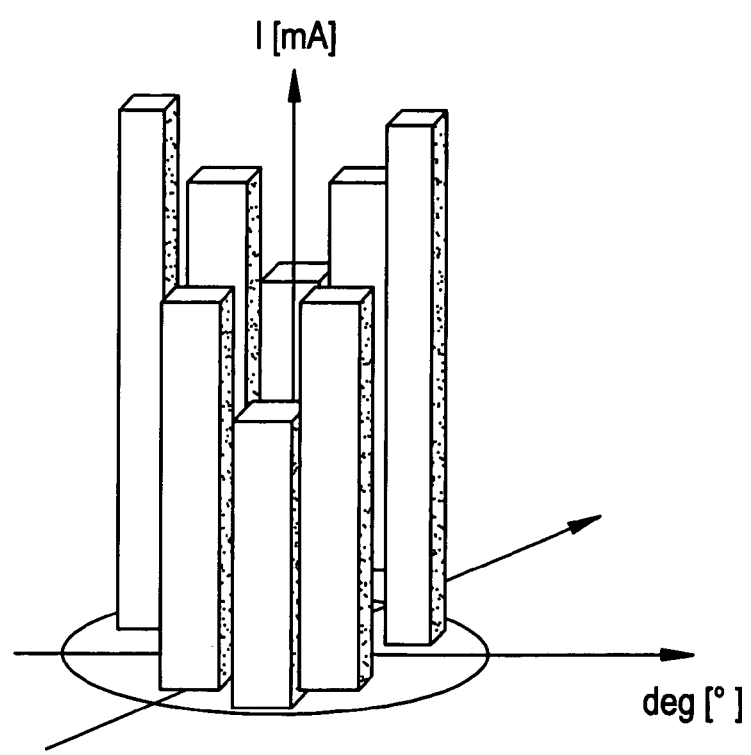
FIG. 8 shows a graph presenting another example of display of tube current values in association with positions in the direction of rotation of the scanner gantry 2 included in the X-ray CT system 1 shown in FIG. 1.

FIG. 8 shows a bar graph presenting another example of display of tube current values associated with positions on a plane of rotation on which the scanner gantry is rotated. As shown in FIG. 8, whether a tube current value is large or small is indicated with the length of a bar, and tube current values are displayed in association with respective angles of rotation.

Otherwise, a tube current value may be displayed in the form of a shade of a color, and tube current values may be displayed in association with respective angles of rotation, though this display is not illustrated.

According to the X-ray CT system of the present embodiment, control values with which X-rays to be irradiated from the X-ray tube and which are calculated in association with positions in the scanning direction or the direction of rotation of the scanner gantry, for example, tube current values are displayed in association with image production positions on the display device. This contributes to improvement of user's maneuverability. Moreover, successive tube current values associated with positions in the scanning direction and the direction of rotation of the scanner gantry are selectively displayed. When the tube current values to be attained during one turn are modified and a scan is performed, the tube current values to be attained during rotation can be checked.

Moreover, a user can finely adjust tube current values displayed on the display device, and check X-ray exposures reduced by the fine adjustment. Thus, reduction ratios of X-ray exposures can be visually grasped. This contributes to improvement of maneuverability and helps check of reduction in an X-ray exposure.

Furthermore, even when reconstructed images and turns are inconsistent with each other during a helical scan or the like, successive tube current values associated with positions in the direction of rotation of the scanner gantry can be checked. Therefore, tube current values associated with images can be checked. Moreover, reduction ratios accompanying tube current values, an absorption dose, a radiation field width, and other information can be displayed simultaneously. This leads to improved working efficiency.

According to the tomography method of the present embodiment, successive tube current values associated with positions in a scanning direction and the direction of rotation of the scanner gantry are selectively displayed. This helps check tube current values during rotation.

Moreover, since tube current values displayed on the display device can be finely adjusted, X-ray exposures can be reduced. Moreover, since reduction ratios of X-ray exposures can be visually checked, maneuverability improves. Even when reconstructed images and turns are inconsistent with each other during a helical scan or the like, tube current values associated with the images can be checked.

A radiation tomography system in accordance with the present invention and a tomography method adapted to the radiation tomography system are not limited to the aforesaid embodiments.

For example, a control value is not limited to a tube current value but may be any parameter as long as a radiation exposure can be controlled based on the parameter. Moreover, a permissible range is determined for each of an absorption dose and a radiation field width, and the absorption dose and radiation field width are calculated. Alternatively, one of the absorption dose and radiation field width may be calculated. Furthermore, the aforesaid settings can be modified for each scan. The scanner gantry is moved for every scan of a subject. Instead, the radiographic table may be moved in the body-axis direction of a subject in order to scan the subject.

Other various modifications can be made without a departure from the gist of the present invention.

Many widely different embodiments of the invention may be configured without departing from the spirit and the scope of the present invention. It should be understood that the present invention is not limited to the specific embodiments described in the specification, except as defined in the appended claims.

What is claimed is:

1. A radiation tomography system including a radiation source and a radiation detector opposed to said radiation source with a subject between them, comprising:
   a scanning device for scanning said subject by moving at least one of said radiation source and radiation detector while rotating it about said subject;
   a control value calculating device for calculating a control value with which an exposure of a radiation emanating from said radiation source is controlled;
   a display device for displaying at least one of control values, which are calculated in association with positions in the direction of rotation in which said scanning device is rotated, and control values, which are calculated in association with positions in the direction of a body axis linking said subject's head and said subject's tiptoe, in relation to the respective pieces of positional information on said subject;
   an adjusting device for adjusting said control values displayed on said display device; and
   a reduction ratio calculating device for comparing said control values displayed on said display device with succeedingly adjusted control values so as to calculate reduction ratios.

2. A radiation tomography system according to claim 1, wherein a continuous change of said control values is displayed on said display device.

3. A radiation tomography system according to claim 1, wherein said control values associated with positions in the direction of rotation of said scanning device and said control values associated with positions in the body-axis direction are displayed on said display device.

4. A radiation tomography system according to claim 1, wherein said calculated reduction ratios are selectively displayed on said display device.

5. A radiation tomography system according to claim 1, wherein at least one of a maximum control value and a minimum control value to be attained during one scan is displayed on said display device.

6. A radiation tomography system according to claim 1, wherein at least one of a maximum control value and a minimum control value attained during one turn made by said scanning device is displayed on said display device.

7. A radiation tomography system according to claim 5, wherein said adjusting device adjusts at least one of the maximum control value and minimum control value displayed on said display device.

8. A radiation tomography system according to claim 1, wherein at least one of an absorption dose and a width of a radiation field determined with said control values is displayed on said display device.

9. A radiation tomography system according to claim 8, further comprising:
    a permissible range designating device for designating a permissible range for at least one of said absorption dose and radiation field width; and
    an absorption dose/radiation field width calculating device for calculating at least one of said absorption dose and radiation field width based on said control values according to a range designated by said designating device,
    wherein at least one of said calculated absorption dose and radiation field width is displayed on said display device.

10. A radiation tomography system according to claim 1, wherein said scanning device adopts X-rays as a radiation.

11. A radiation tomography system according to claim 1, wherein said scanning device controls said radiation exposures using tube current values or tube voltage values as said control values.

12. A tomography method for a radiation tomography system including a radiation source and a radiation detector opposed to said radiation source with a subject between them, said tomography method comprising the steps of:
    calculating a control value with which an exposure of a radiation emanating from said radiation source is controlled;
    displaying a change of calculated control values in association with pieces of positional information on said subject in at least one of the direction of rotation in which said radiation source and radiation detector are rotated or the direction of a body axis linking said subject's head and said subject's tiptoe;
    adjusting the calculated control values;
    comparing the calculated control values with succeedingly adjusted control values so as to calculate reduction ratios; and
    scanning said subject by moving at least one of said radiation source and radiation detector while rotating it about said subject.

13. A tomography method according to claim 12, wherein said change of control values is continuously displayed at said displaying step.

14. A tomography method according to claim 12, wherein said adjusting said calculated control values is interposed between said displaying step and said scanning step.

15. A tomography method according to claim 12, wherein said comparing said calculated control values is performed between said adjusting step and said scanning step.

16. A tomography method according to claim 14, wherein: at said displaying step, at least one of a maximum control value and a minimum control value is displayed; and at said adjusting step, at least one of the maximum control value and minimum control value displayed on a display device is adjusted.

17. A tomography method according to claim 12, wherein at said calculating step, a value of a tube current or a tube voltage to be applied to said radiation source is calculated as a control value.

* * * * *